US 8,499,851 B2
Aug. 6, 2013

(12) United States Patent
Hata

(10) Patent No.: US 8,499,851 B2
(45) Date of Patent: Aug. 6, 2013

(54) FIXED STRUCTURE OF AN ECCENTRIC ROD, AND VIBRATION GENERATOR

(75) Inventor: Yasunori Hata, Uji (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 13/554,556

(22) Filed: Jul. 20, 2012

(65) Prior Publication Data
US 2012/0279739 A1 Nov. 8, 2012

Related U.S. Application Data

(63) Continuation of application No. PCT/JP2011/053274, filed on Feb. 16, 2011.

(30) Foreign Application Priority Data

Feb. 26, 2010 (JP) ................................. 2010-043068

(51) Int. Cl.
*A46B 13/02* (2006.01)
(52) U.S. Cl.
USPC ................ 173/49; 15/22.2; 15/22.1; 433/122
(58) Field of Classification Search
USPC .............. 173/49, 217, DIG. 2; 15/22.1, 22.2, 15/23, 28, 167.1; 433/122; 310/81, 50
See application file for complete search history.

(56) References Cited

U.S. PATENT DOCUMENTS

| 2,282,700 A * | 5/1942 | Bobbroff ........................ 15/22.1 |
| 5,974,613 A * | 11/1999 | Herzog ........................... 15/22.1 |
| 5,987,681 A * | 11/1999 | Hahn et al. ..................... 15/22.1 |
| 6,195,828 B1 * | 3/2001 | Fritsch ............................ 15/22.1 |
| 6,766,548 B1 * | 7/2004 | Lukas et al. .................... 15/22.1 |
| 7,067,945 B2 * | 6/2006 | Grez et al. ....................... 310/50 |
| 7,725,973 B2 * | 6/2010 | Blaustein et al. ............... 15/22.2 |
| 2005/0271997 A1 * | 12/2005 | Mikami et al. ................... 433/29 |
| 2005/0273953 A1 * | 12/2005 | Chan ............................... 15/22.1 |
| 2010/0269275 A1 * | 10/2010 | Shimoyama et al. ............ 15/22.1 |

FOREIGN PATENT DOCUMENTS

| JP | A-2001-521426 | 11/2001 |
| JP | A-2008-80099 | 4/2008 |
| JP | A-2009-240155 | 10/2009 |

OTHER PUBLICATIONS

Mar. 22, 2011 International Search Report issued in International Patent Application No. PCT/JP2011/053274.

* cited by examiner

*Primary Examiner* — Alexandra Elve
*Assistant Examiner* — Andrew M Tecco
(74) *Attorney, Agent, or Firm* — Oliff & Berridge, PLC

(57) ABSTRACT

An electric toothbrush as a vibration generator is provided with a case, a motor, an eccentric rod, a stem, and an oral hygiene member. The eccentric rod has an eccentric weight portion and a rod portion connected to a drive shaft of the motor. The angle between the first central axis of the eccentric weight portion and an extension line, defined by extending the second central axis of the rod portion towards the eccentric weight portion, is greater than 0 degrees and equal to or less than approximately 10 degrees in a state in which one end of the eccentric rod is not inserted into a shaft receiving portion. In this way, a fixed structure of an eccentric rod and a vibration generator are obtained which reduce noise generated by vibration when run at high as well as at low rotation speeds.

6 Claims, 7 Drawing Sheets

FIXED STRUCTURE OF AN ECCENTRIC ROD, AND VIBRATION GENERATOR

This is continuation of application Ser. No. PCT/JP2011/053274 filed Feb. 16, 2011, the contents of which are incorporated herein by reference.

BACKGROUND OF THE INVENTION

1. Field of the Invention

The present invention relates to a fixed structure of an eccentric rod and a vibration generator, and more particularly, it relates to a fixed structure of an eccentric rod generating vibration by rotation of the eccentric rod and a vibration generator.

2. Description of the Background Art

With reference to FIGS. 8 and 9, an electric toothbrush 1 is described as an example of a vibration generator. Electric toothbrush 1 employs a general fixed structure of an eccentric rod. A structure similar to electric toothbrush 1 is disclosed in Japanese Patent Laying-Open No. 2009-240155 (Patent Document 1).

Mainly referring to FIG. 9, general electric toothbrush 1 includes a case 10, a motor 20, an eccentric rod 30, a stem 40 and an oral hygiene member 50. Case 10 is tabularly formed. Case 10 is grasped by the user of electric toothbrush 1. An operating portion 13 is provided on the surface of case 1.

Motor 20 is stored in a portion close to a first end 11 of case 10. Motor 20 has a driving shaft 21. Motor 20 is connected to a prescribed power source (not shown) stored in case 10, in order to rotate driving shaft 21. Eccentric rod 30 is formed substantially in a bar-shaped manner. Eccentric rod 30 has a weight portion 33$b$. The barycentric position of weight portion 33$b$ deviates from a central axis 30$t$ of eccentric rod 30 outward (downward in the plane of FIG. 9). In other words, weight portion 33$b$ is eccentric to central axis 30$t$ of eccentric rod 30. The side of a second end 32 of eccentric rod 30 is connected to driving shaft 21.

Stem 40 is formed in a cap-shaped manner. A bearing portion 44 is provided inside a portion of stem 40 closer to a first end 41. A first end 31 of eccentric rod 30 is inserted into bearing portion 44. Stem 40 is mounted on the side of case 10 to cover eccentric rod 30. Oral hygiene member 50 has a tubular portion 51 and a toothbrushing portion 52. Tubular portion 51 of oral hygiene member 50 is mounted on the outer side of stem 40.

Action of electric toothbrush 1 constituted in the aforementioned manner is described. The user operates operating portion 13 to drive motor 20. Motor 20 rotates driving shaft 21. Eccentric rod 30 rotates integrally with driving shaft 21, due to power transmitted from driving shaft 21.

Weight portion 33$b$ rotates on central axis 30$t$, whereby centrifugal force is generated around central axis 30$t$. This centrifugal force vibrates stem 40. The vibration of stem 40 is transmitted to toothbrushing portion 52 through tubular portion 51 of oral hygiene member 50. Thus, toothbrushing portion 52 vibrates.

SUMMARY OF THE INVENTION

Referring to FIG. 10, stem 40 is mounted on the side of case 10 while holding eccentric rod 30 in the fixed structure of an eccentric rod or the vibration generator such as electric toothbrush 1. Stem 40 is so mounted on the side of case 10 that a reference axis 40$t$ connecting bearing portion 44 of stem 40 and driving shaft 21 of motor 20 with each other is defined.

In the fixed structure of an eccentric rod or the vibration generator such as electric toothbrush 1, on the other hand, central axis 30$t$ of eccentric rod 30 as a whole is linearly formed. Stem 40 is so mounted on case 10 while holding eccentric rod 30 that central axis 30$t$ of eccentric rod 30 and reference axis 40$t$ are arranged on substantially identical straight lines (see the lower side in FIG. 10).

In a case of driving electric toothbrush 1 (motor 20) at a low rotational frequency, the magnitude of a sound generated by vibration of electric toothbrush 1 is small, In a case of driving electric toothbrush 1 at a relatively high rotational frequency (at least about 30000 spm (Strokes per minute), for example), however, the magnitude of a sound generated by vibration of electric toothbrush 1 enlarges.

The present invention aims at providing a fixed structure of an eccentric rod and a vibration generator each capable of reducing the magnitude of a sound generated by vibration when driven not only at a low rotational frequency but also at a high rotational frequency.

A fixed structure of an eccentric rod according to the present invention is a fixed structure of an eccentric rod employed for a vibration generator and includes a rotation driving means having a driving shaft, a substantially bar-shaped eccentric rod, having an eccentric weight portion on the side of a first end and having a rod portion connected to the aforementioned driving shaft on the side of a second end, rotating by power transmitted from the aforementioned rotation driving means through the aforementioned driving shaft, and a vibrating portion, having a bearing portion inside a portion closer to a first end so that the aforementioned first end of the aforementioned eccentric rod is inserted into the aforementioned bearing portion, arranged to cover the aforementioned eccentric rod, while the aforementioned eccentric weight portion has a first central axis extending along the longitudinal direction of the aforementioned eccentric weight portion, the aforementioned rod portion has a second central axis extending along the longitudinal direction of the aforementioned rod portion, an extension line is defined by extending the aforementioned second central axis toward the side of the aforementioned eccentric weight portion, an angle between the aforementioned first central axis of the aforementioned eccentric weight portion and the aforementioned extension line is greater than 0° and not more than about 10° in a state where the aforementioned first end of the aforementioned eccentric rod is not inserted into the aforementioned bearing portion, and the aforementioned first end of the aforementioned eccentric rod is so inserted into the aforementioned bearing portion that the aforementioned eccentric rod is so fixed that the aforementioned first end of the aforementioned eccentric rod regularly urges the inner peripheral surface of the aforementioned bearing portion.

In another mode of the fixed structure of an eccentric rod according to the aforementioned invention, the angle between the aforementioned first central axis of the aforementioned eccentric weight portion and the aforementioned extension line is at least about 2.0° and not more than about 5.0° in the state where the aforementioned first end of the aforementioned eccentric rod is not inserted into the aforementioned bearing portion.

In still another mode of the fixed structure of an eccentric rod according to the aforementioned invention, the aforementioned rod portion is integrally constituted of a substantially columnar rod connector fixing the aforementioned eccentric weight portion to the side of a first end and a shaft connecting portion mounted on the side of a second end of the aforementioned rod connector and connected to the aforementioned driving shaft, and a substantially columnar neck portion relatively smaller in diameter than the remaining portions is formed between the aforementioned first end of the aforementioned rod connector and the aforementioned second end of the aforementioned rod connector.

In a further mode of the fixed structure of an eccentric rod according to the aforementioned invention, the material for the aforementioned rod connector is polyacetal.

In a further mode of the fixed structure of an eccentric rod according to the aforementioned invention, the aforementioned eccentric weight portion and the aforementioned rod portion are integrally molded.

A vibration generator according to the present invention includes the fixed structure of an eccentric rod described in any of the above.

According to the present invention, it becomes possible to obtain a fixed structure of an eccentric rod and a vibration generator each capable of reducing the magnitude of a sound generated by vibration when driven not only at a low rotational frequency but also at a high rotational frequency.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
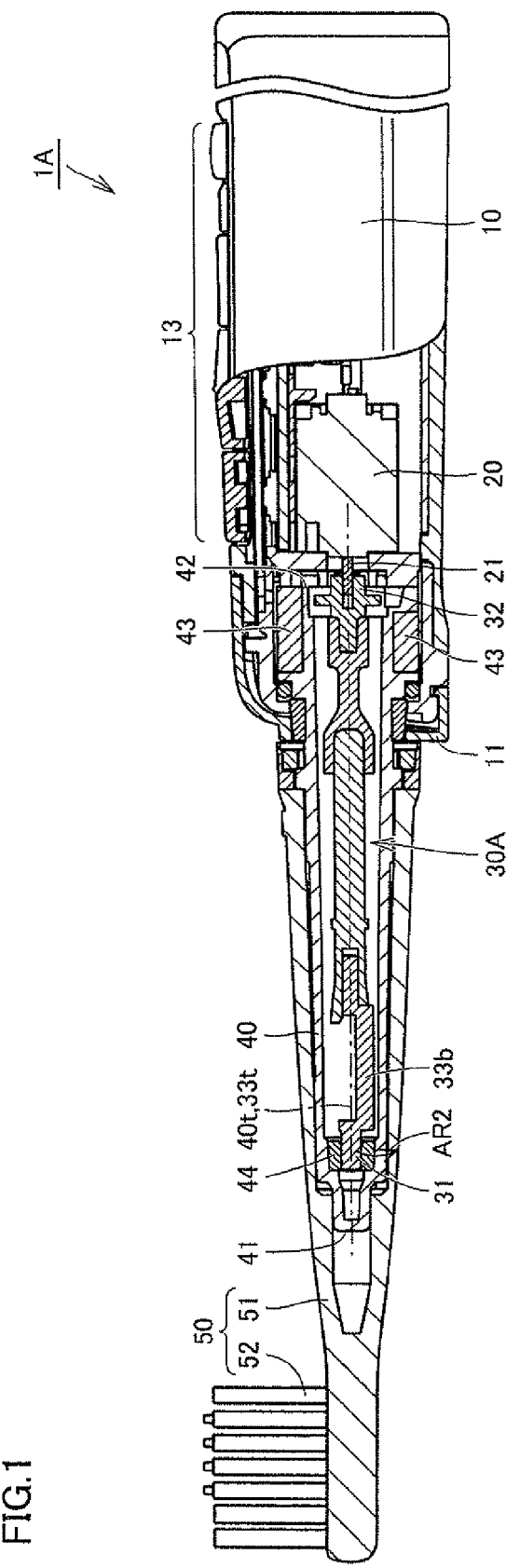
FIG. 1 is a sectional view (partial side elevational view) showing the overall structure of an electric toothbrush according to a first embodiment.

Embodiments based on the present invention are now described with reference to the drawings. Each of the following embodiments is described on the basis of an electric toothbrush generating vibration by rotation of a rotor as an example of a fixed structure of an eccentric rod or a vibration generator. In a case of mentioning a number, an amount or the like in each of the following embodiments, the range of the present invention is not necessarily restricted to the number, the amount or the like, unless specifically described. In each of the embodiments described below, identical reference numerals are assigned to the same components or corresponding components, and redundant description may not be repeated.

First Embodiment

An electric toothbrush 1A according to this embodiment is described with reference to FIGS. 1 to 3.

(Structure)

Referring to FIG. 1, electric toothbrush 1A includes a case 10, a motor 20 (rotation driving means), an eccentric rod 30A, a stem 40 (vibrating portion) and an oral hygiene member 50. Case 10, motor 20, stem 40 and oral hygiene member 50 are constituted similarly to those of aforementioned electric toothbrush 1. A bearing portion 44 provided inside a portion of stem 40 closer to a first end 41 may be constituted integrally with stem 40, or may be constituted as a component different from stem 40.

The material for case 10 is ABS resin (Acrylonitrile-Butadiene-Styrene copolymer synthetic resin), for example. The material for stem 40 is polycarbonate, for example. The material for a fixed member 43 annularly provided on the side of a second end 42 of stem 40 is suitably prepared from elastomer. The material for a tubular portion 51 of oral hygiene member 50 is polypropylene, for example. The material for a toothbrushing portion 52 of oral hygiene member 50 is nylon (piliform), for example. Oral hygiene member 50 in this embodiment is a brushlike member. Oral hygiene member 50 may be a silicon piece group for massage or the like.

Figure 2:
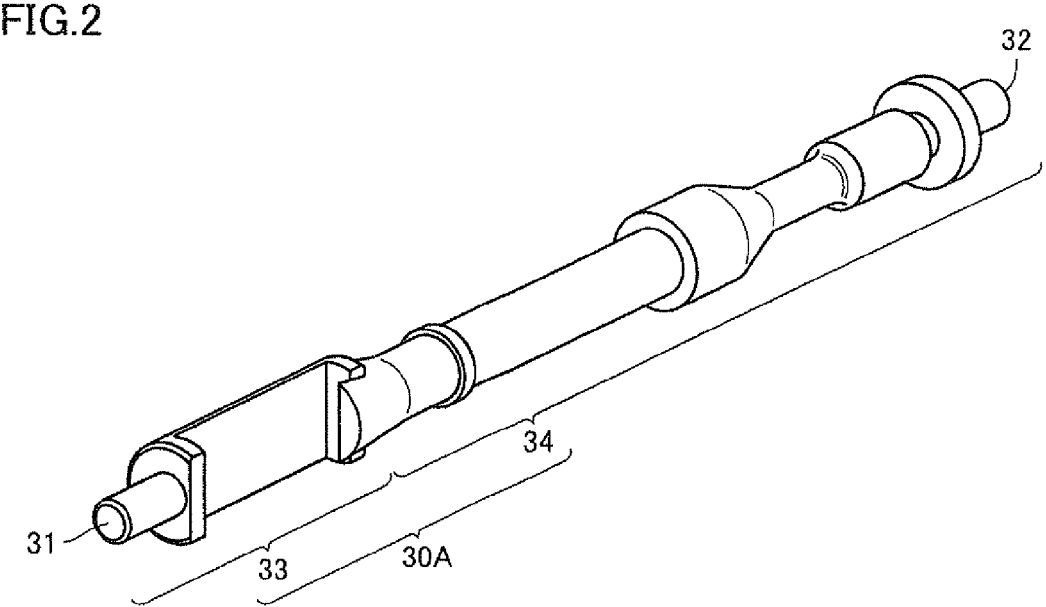
FIG. 2 is a perspective view showing an eccentric rod related to the electric toothbrush according to the first embodiment.

Referring to FIG. 2, eccentric rod 30A is formed substantially in a bar-shaped manner. Eccentric rod 30A has an eccentric weight portion 33 on the side of first end 31, and has a rod portion 34 on the side of second end 32.

Figure 3:
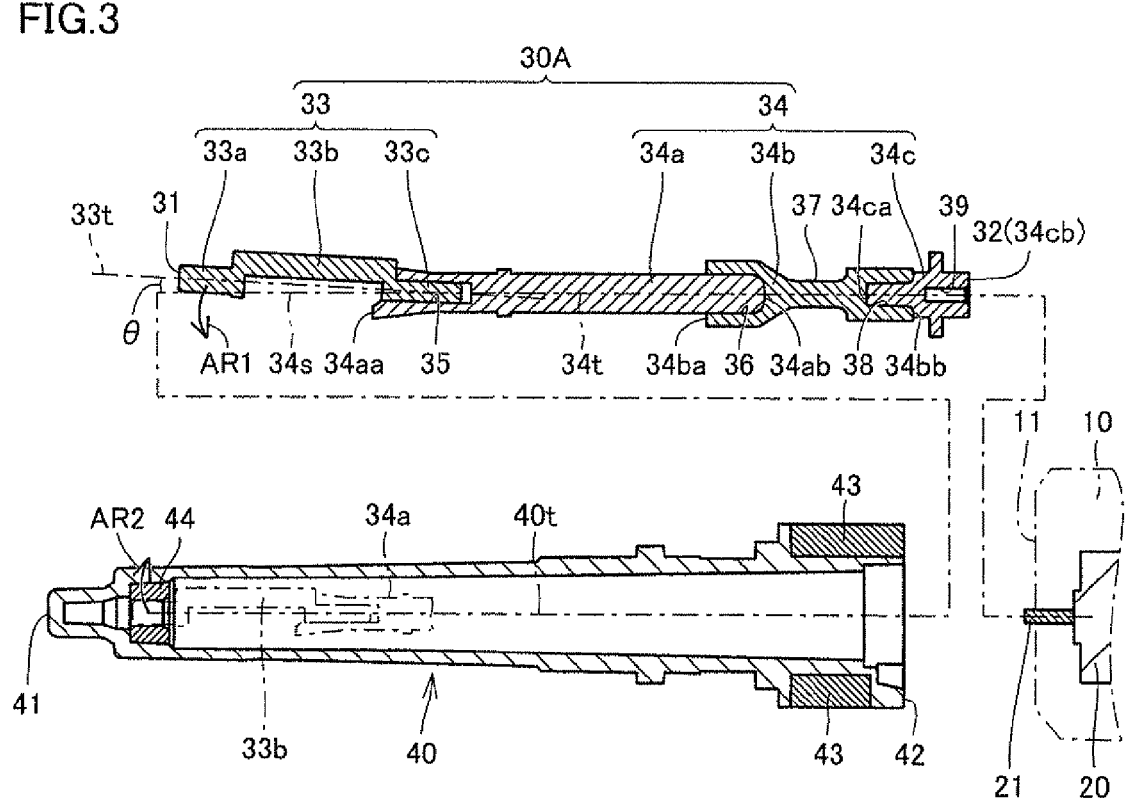
FIG. 3 is a sectional view (assembly drawing) showing a case, a motor, the eccentric rod and a stem related to the electric toothbrush according to the first embodiment.

Referring to FIG. 3, eccentric weight portion 33 is integrally constituted of a columnar insertional portion 33a, a weight portion 33b substantially C-shaped in section and a connecting portion 33c. The material for eccentric weight portion 33 is phosphor bronze, for example. Stem 40 is mounted on the side of case 10 while holding eccentric rod 30A, whereby insertional portion 33a is inserted into bearing portion 44 of stem 40 (see the lower side in FIG. 3). Stem 40 may be mounted on an inner case stored in case 10 for storing a substrate, a motor and the like.

In the longitudinal direction of eccentric weight portion 33, the central axis of insertional portion 33a and the central axis of connecting portion 33e are positioned on substantially identical straight lines. The central axis of insertional portion 33a and the central axis of connecting portion 33c define a first central axis 33t extending along the longitudinal direction of eccentric weight portion 33. The barycentric position of weight portion 33b deviates from first central axis 33t outward (upward in the plane of FIG. 3). In other words, weight portion 33b is eccentric to first central axis 33t.

Rod portion 34 is constituted of a substantially columnar upper rod connector 34a, a substantially columnar (sectionally substantially H-shaped) lower rod connector 34b and a shaft connecting portion 34c. Upper rod connector 34a (except a portion on the side of a first end 34aa), lower rod connector 34b and shaft connecting portion 34c are axisymmetrically formed with respect to a second central axis 34t (details are described later). The term "axisymmetrically" denotes that sectional shapes orthogonal to second central axis 34t are point-symmetrical with respect to second central axis 34t.

The material for upper rod connector 34a and shaft connecting portion 34c is polypropylene, for example. Elastomer or another member having elasticity, for example, can be employed as the material for lower rod connector 34b.

A recess portion 35 is formed on the side of first end 34aa of upper rod connector 34. Connecting portion 33c of eccentric weight portion 33 is fitted into recess portion 35. A recess portion 36 is formed on the side of a first end 34ba of lower rod connector 34b. A second end 34ab of upper rod connector 34a is fitted into recess portion 36. A recess portion 38 is formed on the side of a second end 34bb of lower rod connector 34b. A first end 34ca of shaft connecting portion 34c is fitted into recess portion 38. Upper rod connector 34a and shaft connecting portion 34c are so prepared in advance that upper rod connector 34a, shaft connecting portion 34c and lower rod connector 34b are suitably integrated when molding lower rod connector 34b.

A neck portion 37 is formed on a substantially central portion of lower rod connector 34b in the longitudinal direction. Neck portion 37 is formed in a substantially columnar manner as a whole. The diameter of neck portion 37 is smaller than the diameter of upper rod connector 34a. A recess portion 39 is formed on the side of a second end 34cb of shaft connecting portion 34c. Driving shaft 21 of motor 20 is so fitted into recess portion 39 that eccentric rod 30A is connected to driving shaft 21.

The central axis of upper rod connector 34a, the central axis of lower rod connector 34b and the central axis of shaft connecting portion 34c are positioned on substantially identical straight lines. The central axis of upper rod connector 34a, the central axis of lower rod connector 34b and the central axis of shaft connecting portion 34c define second central axis 34t extending along the longitudinal direction of rod portion 34.

An extension line 34s is defined by extending second central axis 34t toward the side of eccentric weight portion 33. In a state where first end 31 of eccentric rod 30A is not inserted into bearing portion 44 (state of eccentric rod 30A shown on the upper side in the plane of FIG. 3), an angle θ of at least about 2.0° and not more than about 5.0° is formed between first central axis 33t of eccentric weight portion 33 and aforementioned extension line 34s.

In other words, eccentric weight portion 33 is so fixed to rod portion 34 that an angle between first central axis 33t of eccentric weight portion 33 and second central axis 34t of rod portion 34 is at least about 175° and not more than about 178°.

(Functions•Effects)

Stem 40 is mounted on the side of case 10 while holding eccentric rod 30A. When insertional portion 33a is inserted into bearing portion 44, the side of first end 31 of eccentric rod 30A rises in a direction shown by arrow AR1 (see the upper side in the plane of FIG. 3).

Referring to FIG. 1 (or the lower side in the plane of FIG. 3), stem 40 is mounted on the side of case 10. Restoring force to be displaced in a direction shown by arrow AR2 is generated on the side of first end 31 of eccentric rod 30A. The outer peripheral surface of insertional portion 33a regularly urges the inner peripheral surface of bearing portion 44 due to this restoring force. In other words, the outer peripheral surface of insertional portion 33a is regularly pressed against the inner peripheral surface of bearing portion 44.

The user operates operating portion 13 to drive motor 20. Motor 20 rotates driving shaft 21. Eccentric rod 30A rotates integrally with driving shaft 21, due to power transmitted from driving shaft 21. When eccentric rod 30A rotates, the outer peripheral surface of insertional portion 33a slides with respect to the inner peripheral surface of bearing portion 44.

According to electric toothbrush 1A, the aforementioned restoring force acts on the side of first end 31 of eccentric rod 30A. Eccentric rod 30A can rotate in a state reliably keeping the contact state between the outer peripheral surface of insertional portion 33a and the inner peripheral surface of bearing portion 44. Also in a case where motor 20 rotates driving shaft 21 at a high speed, the contact state between the outer peripheral surface of insertional portion 33a and the inner peripheral surface of bearing portion 44 can be more excellently kept (as compared with electric toothbrush 1 described at the beginning). In other words, such an opportunity that the outer peripheral surface of insertional portion 33a and the inner peripheral surface of bearing portion 44 come into contact with each other can be more frequently obtained according to electric toothbrush 1A.

When the outer peripheral surface of insertional portion 33a and the inner peripheral surface of bearing portion 44 are in contact with each other, both ends (first end 31 and second end 32) of eccentric rod 30A serve as the so-called fixed ends. Eccentric rod 30A is enabled to stably rotate.

Figure 10:
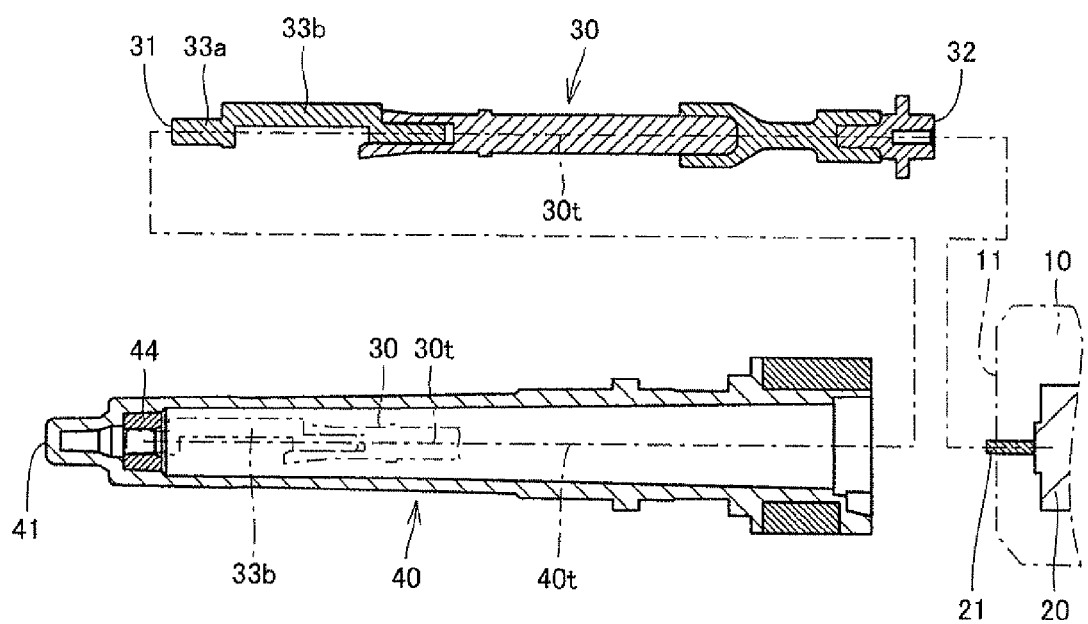
FIG. 10 is a sectional view (assembly drawing) showing a case, a motor, an eccentric rod and a stem related to the general electric toothbrush.

In electric toothbrush 1 (see FIG. 10) described at the beginning, central axis 30t of eccentric rod 30 as a whole is linearly formed. Even if stem 40 is mounted on the side of case 10 while holding eccentric rod 30, the outer peripheral surface of insertional portion 33a does not urge the inner peripheral surface of bearing portion 44 (the outer peripheral surface of insertional portion 33a is not pressed against the inner peripheral surface of bearing portion 44). According to electric toothbrush 1, a contact state between the outer peripheral surface of insertional portion 33a and the inner peripheral surface of bearing portion 44 cannot be kept in a case where motor 20 rotates driving shaft 21 at a high speed. Such a floppy sound is generated that the outer peripheral surface of insertional portion 33a hits the inner peripheral surface of bearing portion 44. Eccentric rod 30 cannot stably rotate. As a result, the magnitude of a sound generated by vibration of eccentric rod 30 enlarges.

In electric toothbrush 1A according to this embodiment, the outer peripheral surface of insertional portion 33a is regularly pressed against the inner peripheral surface of bearing portion 44 when stem 40 is mounted on case 10 while holding eccentric rod 30A, whereby eccentric rod 30A is enabled to stably rotate. Generation of such a floppy sound that the outer peripheral surface of insertional portion 33a hits the inner peripheral surface of bearing portion 44 can be suppressed. As a result, it becomes possible to reduce the magnitude of a sound generated by vibration of eccentric rod 30A.

In electric toothbrush 1A, neck portion 37 substantially columnar as a whole is formed on lower rod connector 34b. The diameter of neck portion 37 is smaller than the diameter of upper rod connector 34a. In neck portion 37, eccentric rod 30A is easy to bend.

Also in a case where eccentric rod 30A so rotates that an excess load acts on eccentric rod 30A, neck portion 37 is so bent that the aforementioned load can be reduced. As a result, it becomes possible to lengthen the endurance of eccentric rod 30A. It becomes possible to more lengthen the endurance of eccentric rod 30A by preparing the material for upper rod connector 34a and shaft connecting portion 34c from polypropylene and preparing the material for lower rod connector 34b from elastomer (softer than polypropylene).

Second Embodiment

An electric toothbrush according to this embodiment is described with reference to FIGS. 4 and 5. The electric toothbrush according to this embodiment and electric toothbrush 1A according to the aforementioned first embodiment are different from each other in an eccentric rod 30B, and similarly constituted as to the remaining points.

Figure 4:
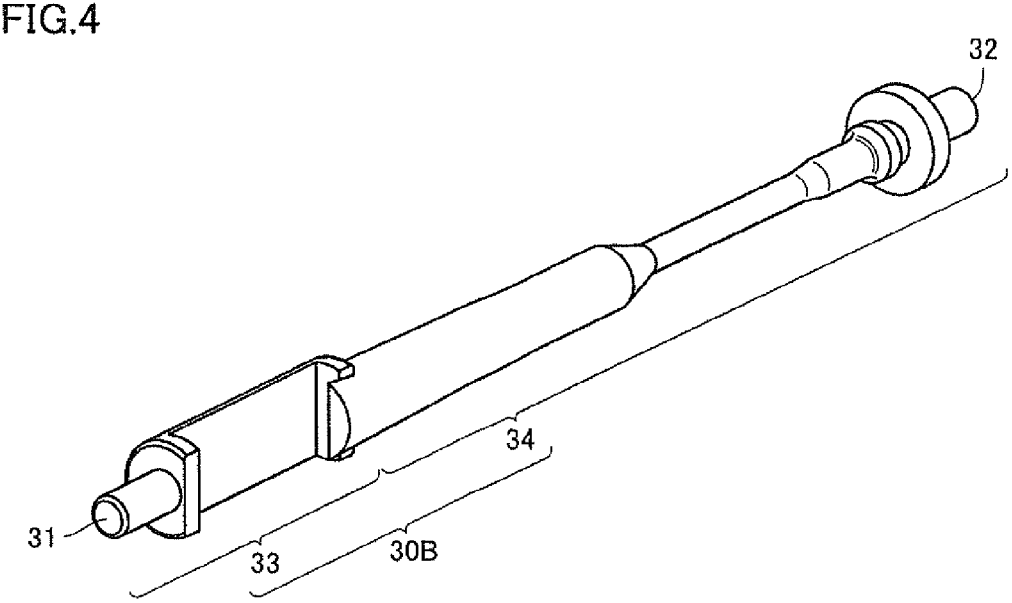
FIG. 4 is a perspective view showing an eccentric rod related to an electric toothbrush according to a second embodiment.

Referring to FIG. 4, eccentric rod 30B is formed substantially in a bar-shaped manner. Eccentric rod 30B has an eccentric weight portion 33 on the side of a first end 31, and has a rod portion 34 on the side of a second end 32.

Figure 5:
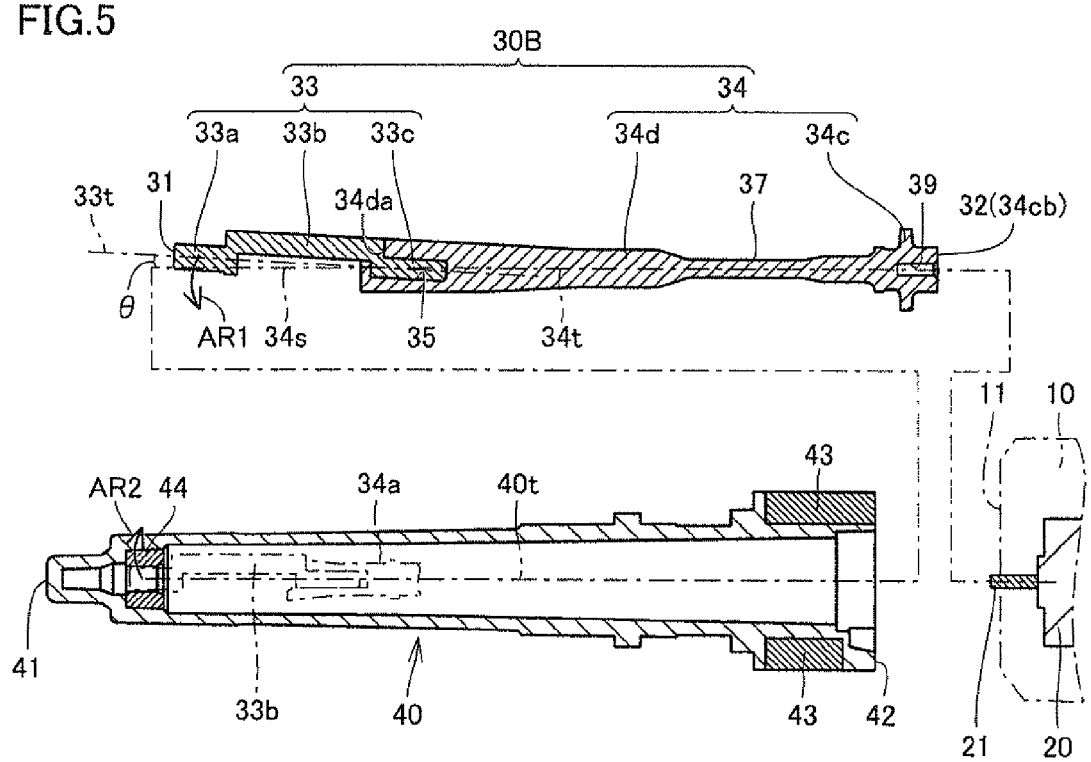
FIG. 5 is a sectional view (assembly drawing) showing a case, a motor, the eccentric rod and a stem related to the electric toothbrush according to the second embodiment.

Referring to FIG. 5, eccentric weight portion 33 is integrally constituted of a columnar insertional portion 33a, a weight portion 33b substantially C-shaped in section and a connecting portion 33c. The material for eccentric weight portion 33 is phosphor bronze, for example. A stem 40 is so mounted on a case 10 while holding eccentric rod 30B that a bearing portion 44 of stem 40 is inserted into insertional portion 33a (see the lower side in FIG. 5).

In the longitudinal direction of eccentric weight portion 33, the central axis of insertional portion 33a and the central axis of connecting portion 33c are positioned on the same straight line. The central axis of insertional portion 33a and the central axis of connecting portion 33c define a first central axis 33t extending along the longitudinal direction of eccentric weight portion 33. The barycentric position of weight portion 33b deviates from first central axis 30t outward (upward in the plane of FIG. 5). In other words, weight portion 33b is eccentric to first central axis 33t.

Rod portion 34 is constituted of a substantially columnar rod connector 34d and a shaft connecting portion 34c. Rod connector 34d (except a portion on the side of a first end 31) and shaft connecting portion 34c are axisymmetrically formed with respect to a second central axis 34t (details are described later). Rod connector 34d is suitably so constituted that the diameter thereof gradually decreases up to a neck portion 37 (details are described later) positioned on the right side in the plane of FIG. 5. According to this structure, rod connector 34d is enabled to improve elasticity and durability as compared with a case where the diameter thereof decreases in stages (stepwise) up to neck portion 37.

The material for rod connector 34d and shaft connecting portion 34c is suitably prepared from polyacetal. Rod connector 34d and shaft connecting portion 34c are integrally molded. Rod connector 34d and shaft connecting portion 34c may be constituted as different components.

A recess portion 35 is formed on the side of a first end 34da of rod connector 34d. Connecting portion 33c of eccentric weight portion 33 is fitted into recess portion 35. In a case of constituting (not integrally molding) rod connector 34d and shaft connecting portion 34c as different components, the side of a second end of rod connector 34d and the side of a first end of shaft connecting portion 34c are bonded to each other. Eccentric weight portion 33 and rod connector 34d are suitably integrally molded by resin molding.

In the longitudinal direction of rod connector 34d, neck portion 37 is formed on a portion of a substantially central portion of rod connector 34d closer to the second end (closer to shaft connecting portion 34c). Neck portion 37 is formed in a substantially columnar manner as a whole. The diameter of neck portion 37 is smaller than the diameter of the remaining portion of rod connector 34d. A recess portion 39 is formed on the side of a second end 34cb of shaft connecting portion 34c. Driving shaft 21 of motor 20 is so fitted into recess portion 39 that eccentric rod 30B is connected to driving shaft 21.

The central axis of rod connector 34d and the central axis of shaft connecting portion 34c are positioned on substantially identical straight lines. The central axis of rod connector 34d and the central axis of shaft connecting portion 34c define second central axis 34t extending along the longitudinal direction of rod portion 34.

An extension line 34s is defined by extending second central axis 34t toward the side of eccentric weight portion 33. In a state where first end 31 of eccentric rod 30B is not inserted into bearing portion 44 (state of eccentric rod 30B shown on the upper side in the plane of FIG. 5), an angle θ of at least about 2.0° and not more than about 5.0° is formed between first central axis 33t of eccentric weight portion 33 and aforementioned extension line 34s.

In other words, eccentric weight portion 33 is so fixed to rod portion 34 that an angle between first central axis 33t of eccentric weight portion 33 and second central axis 34t of rod portion 34 is at least about 175° and not more than about 178°.

(Functions•Effects)

Stem 40 is mounted on the side of case 10 while holding eccentric rod 30B. When insertional portion 33a is inserted into bearing portion 44, the side of first end 31 of eccentric rod 30B rises in a direction shown by arrow AR1 (see the upper side in the plane of FIG. 5).

Referring to the lower side in the plane of FIG. 5, stem 40 is mounted on case 10. Restoring force to be displaced in a direction shown by arrow AR2 is generated on the side of first end 31 of eccentric rod 30B. The outer peripheral surface of insertional portion 33a regularly urges the inner peripheral surface of bearing portion 44 due to this restoring force. In other words, the outer peripheral surface of insertional portion 33a is regularly pressed against the inner peripheral surface of bearing portion 44.

In the electric toothbrush according to this embodiment, eccentric rod 30B is enabled to stably rotate, similarly to electric toothbrush 1A according to the aforementioned first embodiment. As a result, it becomes possible to reduce the magnitude of a sound generated by vibration of eccentric rod 30B.

In the electric toothbrush according to this embodiment, neck portion 37 substantially columnar as a whole is formed on rod connector 34d. The diameter of neck portion 37 is smaller than the diameter of the remaining portion of rod connector 34d. In neck portion 37, eccentric rod 30B is easy to bend.

Also in a case where eccentric rod 30B so rotates that an excess load acts on eccentric rod 30B, neck portion 37 is so bent that the aforementioned load can be reduced. As a result, it becomes possible to lengthen the endurance of eccentric rod 30B. It becomes possible to more lengthen the endurance of eccentric rod 30B by preparing the material for rod connector 34d from polyacetal.

Rod portion 34 of eccentric rod 30B in this embodiment is constituted of rod connector 34d and shaft connecting portion 34c as one component (may be constituted of rod connector 34d and shaft connecting portion 34c as two components). On the other hand, rod portion 34 of eccentric rod 30A in the first embodiment is constituted of three components (upper rod connector 34a, lower rod connector 34b and shaft connecting portion 34c). According to the electric toothbrush in this embodiment, it becomes possible to reduce the number of components and the manufacturing cost.

In a case of integrally molding rod connector 34d and eccentric weight portion 33, eccentric weight portion 33 is suitably placed on a prescribed die, to be integrated with rod connector 34d by resin molding. In this case, eccentric weight portion 33 may simply be coaxially formed, whereby the manufacturing cost can be suppressed, and the manufacturing itself is also easy. In a case where rod connector 34d and eccentric weight portion 33 are not integrally molded, on the other hand, it is necessary to fit eccentric weight portion 33 into rod connector 34d. In this case, it is rather difficult to provide a hole on the side of rod connector 34d, and it is necessary to constitute eccentric weight portion 33 in an uncoaxial shape.

[Experimental Results Related to Second Embodiment]

Experimental results related to the second embodiment are described with reference to FIGS. 6 and 7. In the structure of the second embodiment, change (see FIG. 6) of a noise level N of a vibrating sound generated from an electric toothbrush and current consumption IC (A) of the electric toothbrush at a time of varying an angle θ between a first central axis 33t (see FIG. 5) of an eccentric weight portion 33 and an extension line 34s were measured. The noise level denotes a prescribed value calculated on the basis of the frequency, the sound pressure etc. of the vibrating sound.

In the electric toothbrush used for this experiment, the total length of eccentric weight portion 33 is about 23 mm. The total length of a rod portion 34 is about 45 mm. The material for eccentric weight portion 33 is phosphor bronze. The diameter of rod portion 34 is about 3 mm. The diameter of a neck portion 37 in rod portion 34 is about 1.57 mm. The material for rod portion 34 is polyacetal. The diameter of an insertional portion 33a of eccentric weight portion 33 is about 1.98 mm. The diameter of the inner peripheral surface of a bearing portion 44 of a stem 40 is about 2.00 mm. The rotational frequency of a motor 20 is about 33000 spm.

Figure 6:
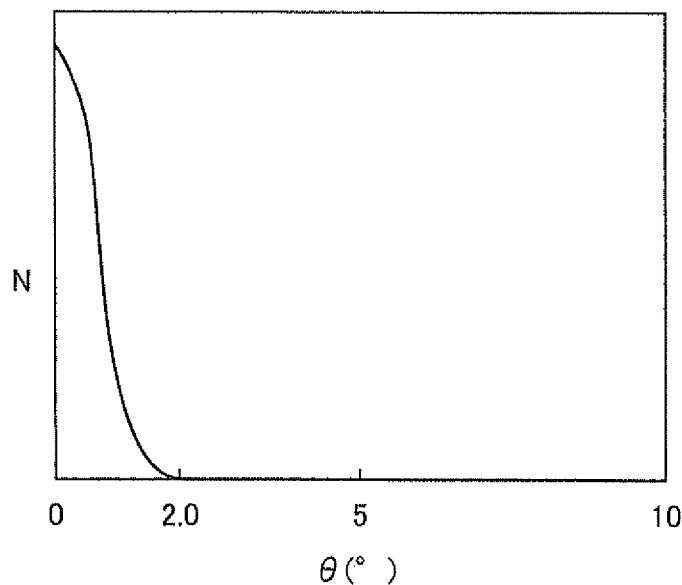
FIG. 6 is a first diagram schematically showing experimental results related to the electric toothbrush according to the second embodiment.

Referring to FIG. 6, the noise level N is high when the angle θ is 0°. It is perceivable that the noise level N abruptly decreases as the angle θ is increased beyond 0°. When the angle θ became at least about 2.0°, the noise level N hardly decreased. When the angle θ got greater than about 10°, it became difficult to assemble an eccentric rod and the stem (bearing portion) while the noise level N kept the decreasing state.

Figure 7:
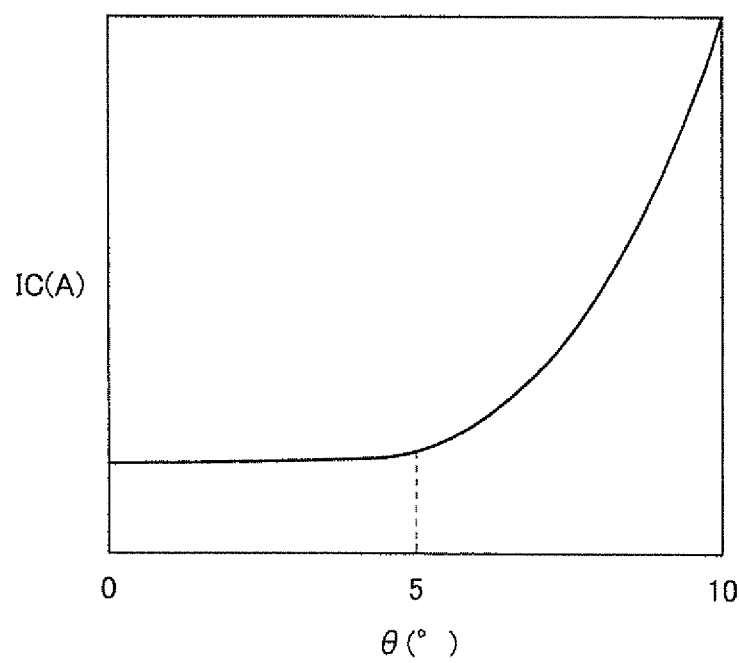
FIG. 7 is a second diagram schematically showing experimental results related to the electric toothbrush according to the second embodiment.
Figure 8:
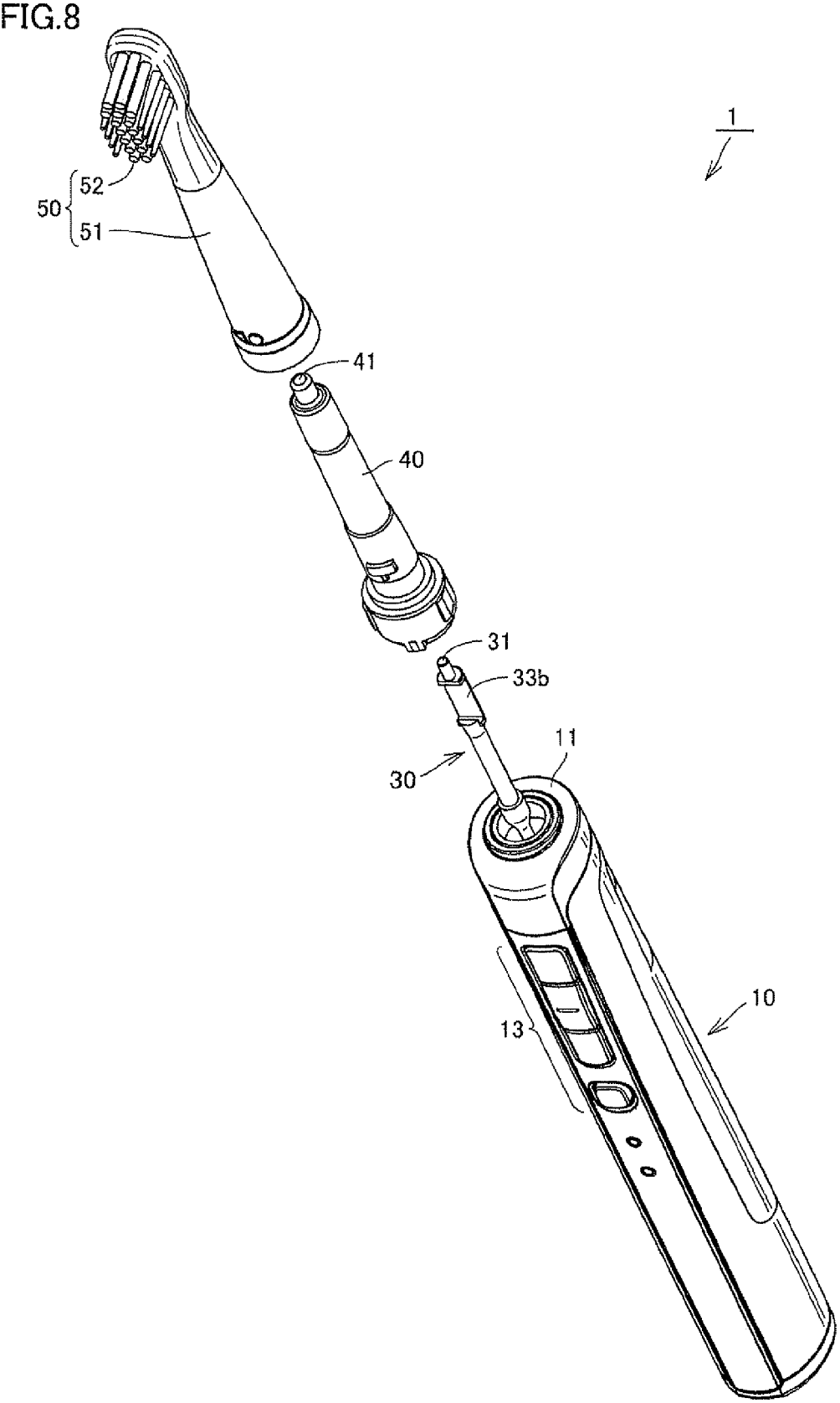
FIG. 8 is a perspective view (assembly drawing) showing the overall structure of a general electric toothbrush.
Figure 9:
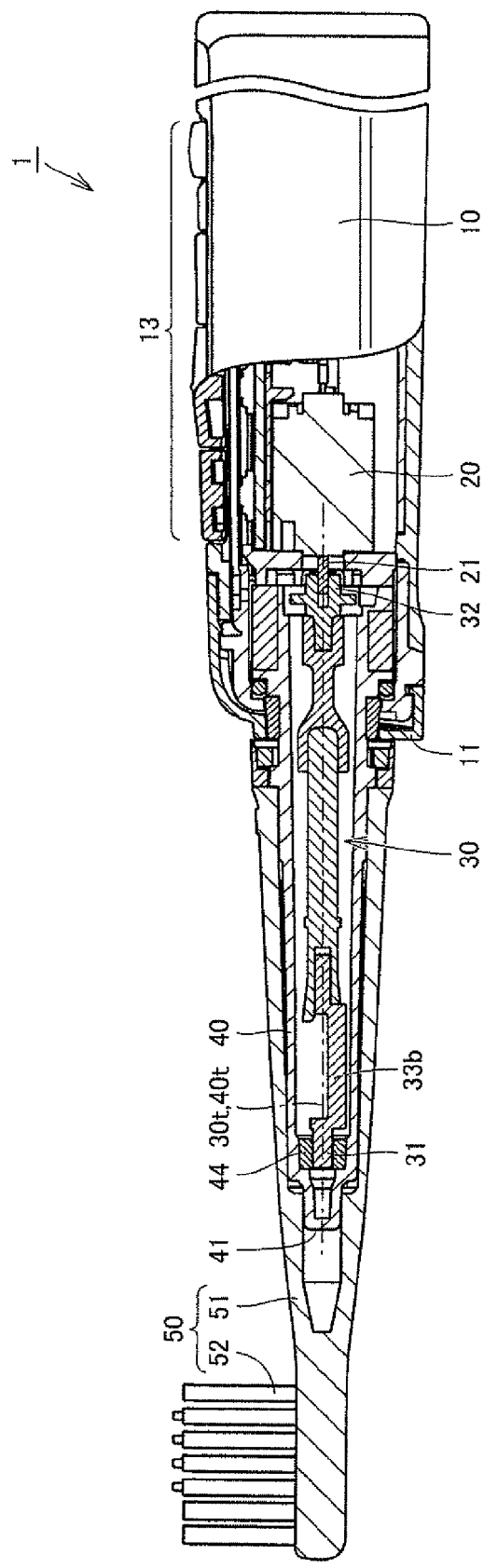
FIG. 9 is a sectional view (partial side elevational view) showing the overall structure of the general electric toothbrush.

Referring to FIG. 7, change was hardly observed in current consumption IC when the angle θ was at least 0° and not more than about 5°. Current consumption IC increased as the angle θ got greater than about 5°.

From the above, it is understood that the angle θ is suitably at least about 2.0° and not more than about 5°. More preferably, it has been understood that the angle θ is suitably at least about 3.0° and not more than about 3.5°.

While a similar experiment was conducted also in the structure of the first embodiment, it has been understood that the angle θ is suitably at least about 2.0° and not more than about 5°. More preferably, it has been understood that the angle θ is suitably at least about 3.0° and not more than about 3.5°.

While the fixed structure of an eccentric rod and the vibration generator have been described with reference to the electric toothbrush as each embodiment based on the present invention, the modes disclosed this time must be considered as illustrative and not restrictive in all points. For example, while the electric toothbrush according to each of the aforementioned embodiments has been described with reference to a substantially linearly formed substantially cylindrical case, the present invention is not restricted to this. The aforementioned case may be constituted to be partially bent on an intermediate portion so that the user can more easily grasp the same.

While each of the aforementioned embodiments has been described on the basis such a mode that the whole of oral hygiene member 50 covering stem 40 is exchangeable as the structure of the so-called brush-exchange type electric toothbrush, the present invention is not restricted to this. The present invention is also applicable to such a structure that oral hygiene member 50 has no tubular portion 51 (such a structure that tubular portion 51 and stem 40 are integrated with each other) and to such a mode that only toothbrushing portion 52 and the vicinity of a pedestal portion where toothbrushing portion 52 is embedded are exchangeable. The present invention is also applicable to such a structure that oral hygiene member 50 has no tubular portion 51 and such a mode that toothbrushing portion 52 is directly provided on stem 40 (the toothbrushing portion is unexchangeable).

The fixed structure of an eccentric rod and the vibration generator based on the present invention are not restricted to the electric toothbrush, but also applicable to a scalp brush provided with a vibrator function, an electric dental treatment appliance or an electric tool, for example. The range of the present invention is shown by the scope of claims for patent, and it is intended that all modifications within the meaning and range equivalent to the scope of claims for patent are included.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A fixed structure of an eccentric rod employed for a vibration generator, comprising:
   a rotation driving means having a driving shaft;
   a bar-shaped eccentric rod, having an eccentric weight portion on the side of a first end and having a rod portion connected to the driving shaft on the side of a second end, rotating by power transmitted from the rotation driving means through the driving shaft; and
   a vibrating portion, having a bearing portion inside a first end so that the first end of the eccentric rod is inserted into the bearing portion, arranged to cover the eccentric rod, wherein
   the eccentric weight portion has an insertional portion inserted into the bearing portion, a connecting portion connected to the rod portion, and a weight portion provided between the insertional portion and the connecting portion, the central axis of the insertional portion and the central axis of the connecting portion being positioned on identical straight lines and defining a first central axis extending along the longitudinal direction of the eccentric weight portion,
   the rod portion has a second central axis extending along the longitudinal direction of the rod portion,
   an extension line is defined by extending the second central axis toward the side of the eccentric weight portion,
   the extension line being collinear with the central axis of the insertional portion and the central axis of the connecting portion when the insertional portion is inserted into the bearing portion,
   an angle between the first central axis of the eccentric weight portion and the extension line is greater than 0° and not more than 10° in a state where the first end of the eccentric rod is not inserted into the bearing portion, and
   the first end of the eccentric rod is so inserted into the bearing portion that the eccentric rod is so fixed that the first end of the eccentric rod regularly urges the inner peripheral surface of the bearing portion.

2. The fixed structure of an eccentric rod according to claim 1, wherein
   the angle between the first central axis of the eccentric weight portion and the extension line is at least 2.0° and not more than 5.0° in the state where the first end of the eccentric rod is not inserted into the bearing portion.

3. The fixed structure of an eccentric rod according to claim 1, wherein the rod portion is integrally constituted of a columnar rod connector fixing the eccentric weight portion to the side of an end, a columnar neck portion positioned closer to the driving shaft than the columnar rod connector, and a shaft connecting portion positioned closer to the driving shaft than the columnar neck portion and connected to the driving shaft, and the neck portion has a diameter smaller than diameters of the columnar rod connector and the shaft connecting portion.

4. The fixed structure of an eccentric rod according to claim 3, wherein the material for the rod connector is polyacetal.

5. The fixed structure of an eccentric rod according to claim 1, wherein the eccentric weight portion and the rod portion are integrally molded.

6. A vibration generator, comprising a fixed structure for an eccentric rod employed for the vibration generator, the fixed structure for an eccentric rod including:

a rotation driving means having a driving shaft;

a bar-shaped eccentric rod, having an eccentric weight portion on the side of a first end and having a rod portion connected to the driving shaft on the side of a second end, rotating by power transmitted from the rotation driving means through the driving shaft; and a vibrating portion, having a bearing portion inside a first end so that the first end of the eccentric rod is inserted into the bearing portion, arranged to cover the eccentric rod, wherein the eccentric weight portion has an insertional portion inserted into the bearing portion, a connecting portion connected to the rod portion, and a weight portion provided between the insertional portion and the connecting portion, the central axis of the insertional portion and the central axis of the connecting portion being positioned on identical straight lines and defining a first central axis extending along the longitudinal direction of the eccentric weight portion, the rod portion has a second central axis extending along the longitudinal direction of the rod portion, an extension line is defined by extending the second central axis toward the side of the eccentric weight portion, the extension line being collinear with the central axis of the insertional portion and the central axis of the connecting portion when the insertional portion is inserted into the bearing portion, an angle between the first central axis of the eccentric weight portion and the extension line is greater than 0° and not more than 10° in a state where the first end of the eccentric rod is not inserted into the bearing portion, and the first end of the eccentric rod is so inserted into the bearing portion that the eccentric rod is so fixed that the first end of the eccentric rod regularly urges the inner peripheral surface of the bearing portion.

* * * * *